United States Patent
Davis, Jr. et al.

(10) Patent No.: US 8,018,590 B2
(45) Date of Patent: Sep. 13, 2011

(54) THREE-DIMENSIONAL OPTICAL SENSOR AND SYSTEM FOR COMBUSTION SENSING AND CONTROL

(75) Inventors: Lewis Berkley Davis, Jr., Niskayuna, NY (US); Keith Robert McManus, Clifton Park, NY (US)

(73) Assignee: General Electric Company, Schenectady, NY (US)

(\*) Notice: Subject to any disclaimer, the term of this patent is extended or adjusted under 35 U.S.C. 154(b) by 352 days.

(21) Appl. No.: 12/256,754

(22) Filed: Oct. 23, 2008

(65) Prior Publication Data

US 2010/0103424 A1    Apr. 29, 2010

(51) Int. Cl.
*G01J 3/30* (2006.01)
(52) U.S. Cl. .......................... 356/311; 356/316
(58) Field of Classification Search .......... 356/311–316; 431/14, 75, 76; 348/83
See application file for complete search history.

(56) References Cited

U.S. PATENT DOCUMENTS

| | | | | |
|---|---|---|---|---|
| 5,249,954 A | * | 10/1993 | Allen et al. | 431/14 |
| 5,551,780 A | | 9/1996 | Wintrich et al. | |
| 5,797,736 A | * | 8/1998 | Menguc et al. | 431/75 |
| 6,251,679 B1 | | 6/2001 | Annen et al. | |
| 6,551,094 B2 | * | 4/2003 | Fastnacht et al. | 431/2 |
| 6,640,199 B1 | | 10/2003 | Goldstein et al. | |
| 2009/0122148 A1 | * | 5/2009 | Fife et al. | 348/218.1 |

FOREIGN PATENT DOCUMENTS

DE    19710206 A1    9/1998

OTHER PUBLICATIONS

EP Search Report for EP Application No. EP 09 17 3706; dated Dec. 10, 2009.
Keith Fife, et al., A 3D Multi-Aperture Image Sensor Architecture, Department of Electrical Engineering, Stanford University, Stanford, California.

\* cited by examiner

*Primary Examiner* — L. G Lauchman
(74) *Attorney, Agent, or Firm* — Cantor Colburn LLP

(57) ABSTRACT

A system includes an optical sensor that optically measures and spatially resolves in three dimensions at least one chemical species within a flame produced by a device and a component that correlates the three dimensionally measured at least one chemical species to at least one parameter of the device.

18 Claims, 4 Drawing Sheets

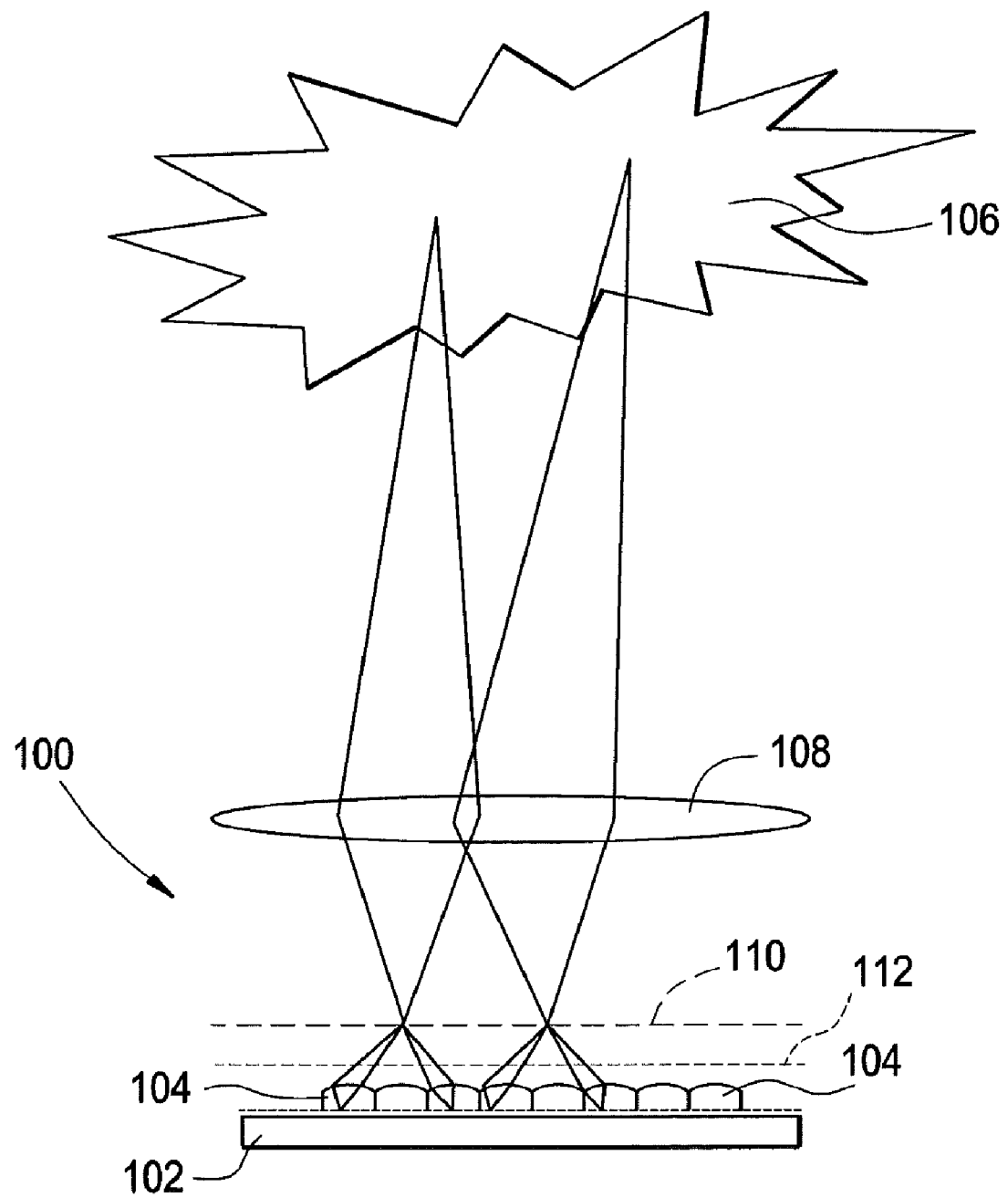

FIG. 2A
FIG. 2B
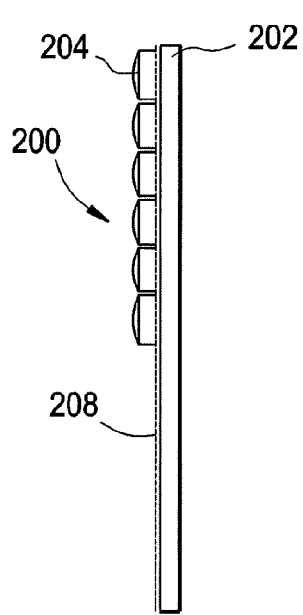
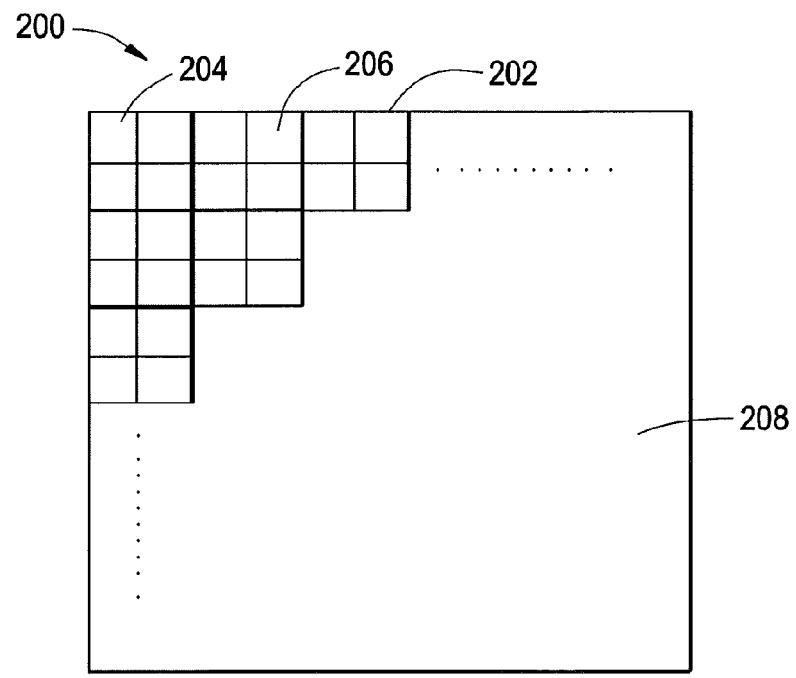

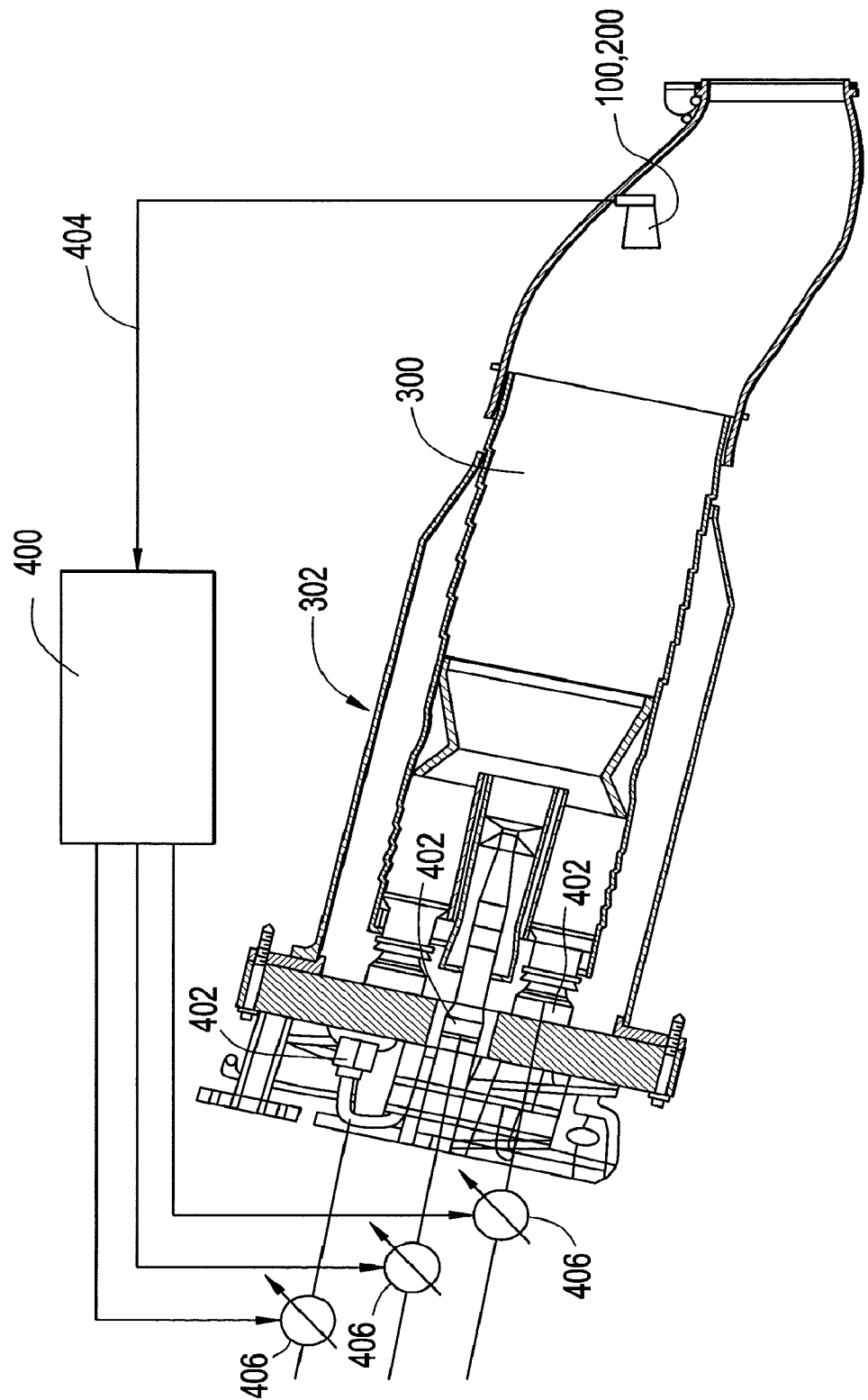

THREE-DIMENSIONAL OPTICAL SENSOR AND SYSTEM FOR COMBUSTION SENSING AND CONTROL

BACKGROUND OF THE INVENTION

The subject matter disclosed herein relates to the optical measurement of light and, more particularly, to an optical sensor that performs three-dimensional, spatially-resolved optical measurements of the flame of a combustor of a gas turbine engine and to a system that utilizes the optical measurements to better control the combustion process.

Optical measurements of flame chemiluminescent light emission are routinely used in premixed gas combustors in gas turbine engines to determine various parameters such as energy or heat release rates and fuel-to-air ratios in such combustors. Placing wavelength filters in front of optical detectors is typically used to identify the partial contribution of the total light emission from each of specific excited-state species, such as $OH^*$, $CH^*$, $C_2^*$ and $CO_2^*$. Ratios of the signals of one or more of these species can then be correlated in a known manner to various combustor parameters such as the fuel-to-air ratio, heat release rate and gas temperature. Previous applications of this measurement technique have used simple optical sensor arrangements and camera systems. A problem with these techniques and systems is their inherent limited spatial resolution. In complex combustion flows, the ability to make spatially resolved measurements in three dimensions is critical to optimizing system performance through improved control of the combustion process.

The use of exhaust temperature spread as a surrogate for combustor chamber-to-chamber variation in fuel-to-air ratio, heat release rate and gas temperature is adequate. However, results can be improved by using optical techniques to observe the flame in each combustor can. A primary issue with using optical methods in these situations has been that they typically provide limited line-of-sight information when what is preferably needed is three-dimensional, spatially-resolved information about the entire flame in each combustor can.

BRIEF DESCRIPTION OF THE INVENTION

According to one aspect of the invention, a system includes an optical sensor that optically measures and spatially resolves in three dimensions at least one chemical species within a flame produced by a device and a component that correlates the three dimensionally measured at least one chemical species to at least one parameter of the device.

According to another aspect of the invention, a method includes optically measuring and spatially resolving in three dimensions at least one chemical species within a flame produced by a device, and correlating the three dimensionally measured at least one chemical species to at least one parameter of the device.

According to yet another aspect of the invention, a system includes an optical sensor that optically measures and spatially resolves in three dimensions at least one chemical species within a flame produced by a combustor, and a device that correlates the three dimensionally measured at least one chemical species to at least one parameter of the combustor.

These and other advantages and features will become more apparent from the following description taken in conjunction with the drawings.

BRIEF DESCRIPTION OF THE DRAWING

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

FIG. 1 illustrates an optical sensor and accompanying optics according to an embodiment of the present invention for measuring the combustion flame in three dimensions in a combustor portion of a gas turbine engine;

FIG. 2, including FIGS. 2A and 2B, are side and top views, respectively, of another embodiment of the present invention for measuring the combustion flame in three dimensions in a combustor portion of a gas turbine engine;

FIG. 4 is side view, partially cutaway, of the sensors of FIGS. 1 or 2 located in the combustor of a gas turbine engine, together with an associated controller and fuel control valves.

Figure 3:
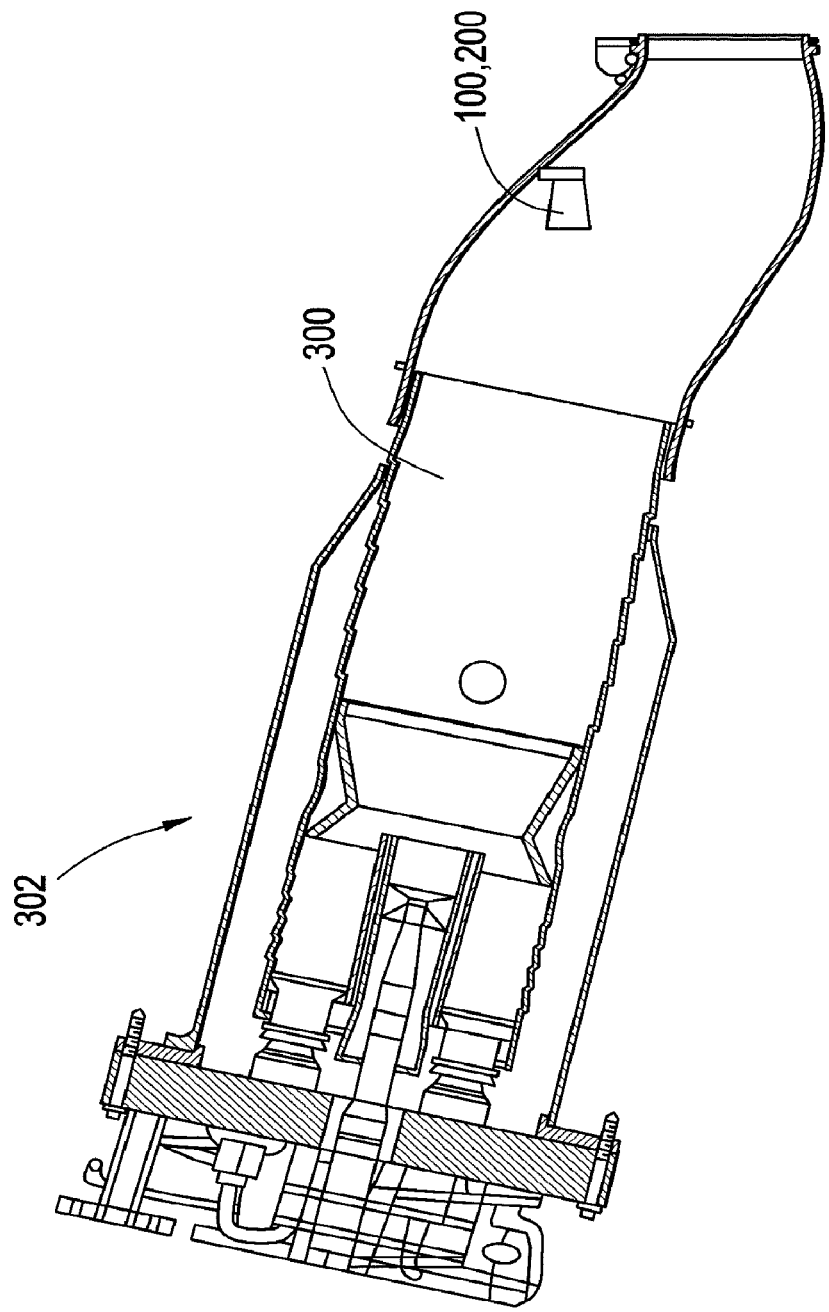
FIG. 3 is a side view, partially cutaway, of the sensors of FIGS. 1 or 2 located in the combustor of a gas turbine engine.

The detailed description explains embodiments of the invention, together with advantages and features, by way of example with reference to the drawings.

DETAILED DESCRIPTION OF THE INVENTION

Referring to FIG. 1, an image sensor 100 according to an embodiment of the invention includes a single sensor array 102 having a plurality of apertures 104 for sensing emitted light at a particular wavelength. The image sensor 100 may be a single wavelength color sensor that provides a three-dimensional mapping of the flame chemiluninescence intensity emitted by a single chemical species from among a number of different such species (e.g., $OH^*$, $CH^*$, $C_2^*$, $CO_2^*$, wherein the asterisk "*" following the molecule name denotes the molecule in an excited state) of the flame within the combustion zone 106 of a combustor (FIGS. 3-4) of a gas turbine engine. The optical image of the flame within the combustion zone 106 is focused not directly onto the apertures 104 in the sensor array 102, but instead is focused by an imaging lens 108 to a focal plane 110 located above the apertures 104. The image is then re-imaged by an optical filter 112 having a single wavelength onto the apertures 104 to form partially overlapping images or fields of view of the combustion zone 106 between the apertures 104. The optical filter 112 (i.e., local optics) may be implemented in a dielectric stack of an integrated circuit using refractive microlenses or diffractive gratings patterned in metal layers. The sensed images of the chemical species may then be combined to form a three-dimensional, spatially-resolved representation of the flame within the combustion zone 106. The multiple perspective views of the image of the flame in the combustion zone 106 allow for the synthesis of a three-dimensional image at a greater spatial resolution that the number of apertures 104 themselves.

In an alternative embodiment of the invention, more than one sensor array 102 may be utilized, with different wavelength filtering capability provided on each array 102. This allows for simultaneous measurement of several different chemical species (e.g., $OH^*$, $CH^*$, $C_2^*$, $CO_2^*$) of the flame within the combustion zone 106, wherein these different chemical species are at different wavelengths. This allows for performing ratiometric measurements between the multiple species. The ratios of at least two different ones of these species can then be correlated in a known manner to arrive at or to derive various combustor parameters such as the fuel-to-air ratio, heat release rate, and gas temperature. In contrast, if a single sensor array 102 is provided with a single wavelength filtering capability, then typically the heat release rate and gas temperature can be correlated or derived from the measured single chemical species.

Referring to FIGS. 2A and 2B, in another embodiment of the image sensor 200 according to the present invention, a two-dimensional array 202 of apertures 204 may be provided. In this embodiment, multiple different filter elements 206 may be deposited directly onto the apertures 204 of the imaging array 202 to allow for multiple different color measurements to be carried out. The array 200 is best seen in the top view (i.e., facing the array) of FIG. 2B. Thin film deposition of, e.g., silicon or silicon carbide, may be used to create a color filter array on a surface 208 of the image sensor 200. Other materials that may be deposited include magnesium fluoride, calcium fluoride and various metal oxides. In the example shown in FIG. 2, there are four different color filters 206 arranged in a square (2×2), and this square pattern is repeated over the entire top surface 208 of the sensor 200. The four different color filters 206 represent the predominant color for each of the chemical species (e.g., OH*, CH*, C2*, CO2*) desired to be measured. Each filter element 206 may have a microlens located above the element, and each group of four color filter elements provides for a multiple wavelength intensity map of the flame over the combustion region 106 (FIG. 1).

FIG. 3 illustrates the three-dimensional combustion image sensor 100, 200 of FIGS. 1 or 2 deployed in a typical combustor 300 that is part of a gas turbine engine 302. In this example, the image sensor 100, 200 may be located in the transition duct downstream from the main combustion region. Each can in a typical combustor 300 of the gas turbine engine 302 may have an image sensor 100, 200 located therein to measure the characteristics of the flame in each can. The image sensor 100, 200 may be integrated with an air- or liquid-cooled mounting bracket, so as to be able to withstand the normally harsh thermal environment. As mentioned, the image sensor 100, 200 provides a three-dimensional, spatially-resolved map of the measured chemical species (e.g., OH*, CH*, C2*, CO2*), and from the measured chemical species various specific combustion parameters, such as fuel-to-air ratio, heat release rate, or gas temperature, may be correlated or derived in a known manner. The output of the image sensor may be provided to a controller 400 (FIG. 4) that correlates the measure chemical species to the specific combustion parameters. In response to the correlated or derived combustion parameters, the controller can vary the flow parameters to the fuel nozzles 402 (FIG. 4) in the combustor 300 to directly affect and balance or improve the combustion process within the gas turbine engine 302.

FIG. 4 illustrates the three-dimensional image sensor 100, 200 of FIGS. 1 or 2 integrated with the gas turbine controller 400. The output signal from the sensor 100, 200 on a line 404 is fed to the controller 400 through an electrical cable or suitable fiber optic connection. The controller 400 processes the image information from the sensor 100, 200 and takes a control action when non-optimal operation of the combustor 300 is detected. In this example, the control action may comprise an adjustment of the individual fuel supply valves 406 that feed the fuel injection nozzles 402 within the fuel injection system of the engine 302. In this way, the combustion process can be improved using the output of the image sensor 100, 200 in a feedback control system. Similarly, to achieve optimum operation, the controller 400 may vary other parameters automatically. These parameters may include, e.g., airflow distribution, diluent injection and fuel nozzle geometry.

Embodiments of the image sensor 100, 200 of the present invention in general provide a three-dimensional, spatially-resolved map of the combustion parameters in a reacting flow.

The image sensor 100, 200 allows for the indirect three-dimensional measurement or correlation of various combustion parameters such as heat release rate, fuel-to-air ratio and gas temperature from the directly measured concentrations of various specific chemical species in the flame of the combustor 300. The sensor 100, 200 includes a multi-aperture imaging device coupled to optical filters to collect light from the flame chemiluminescent emission. The light emission from excited state species such as OH*, CH*, C2* and CO2* is collected on a single, or a multiple multi-aperture array such that three-dimensional, spatially-resolved maps of these concentrations of these species are obtained. The measured three-dimensional, spatially-resolved maps can be correlated with parameters associated with the combustor 300 such as heat release rate, fuel-to-air ratio, and gas temperature in each combustor can. This can be used for combustor health monitoring as well as engineering assessment of the performance of a given combustor design.

A method for monitoring these various combustion parameters (fuel-to-air ratio, heat release rate, temperature, etc.) is part of a combustion monitoring package necessary for closed loop or model based control of a gas turbine combustor 300. Such a package includes a monitor of combustion dynamics, emissions, and fuel-to-air ratio, heat release rate and gas temperature for each combustion chamber or can in a gas turbine engine 302. In the alternative, embodiments of the invention are applicable to annular (i.e., non-can) combustors or afterburners, to measure the characteristics of the flame in these devices. Combustion monitoring is an integral part of advanced controls packages for high performance gas turbine combustors. Elements being monitored include combustion dynamic pressure oscillations, emissions, fuel-to-air ratio, heat release and gas temperature. Embodiments of the present invention provide for relatively greater fidelity in monitoring real time variations in the fuel-to-air ratio, heat release rate and gas temperature between combustion chambers so that fuel and air flow adjustments to each combustor can be made to reduce these variations. This results in relatively lower emissions and greater durability and operability over a wider range of gas turbine operation.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:
1. A system, comprising:
an optical sensor configured to be disposed in a gas turbine engine that optically measures and spatially resolves in three dimensions at least one chemical species within a flame produced by a combustor in the gas turbine engine; and
a component that correlates the three dimensionally measured at least one chemical species to at least one parameter of the combustor.
2. The system of claim 1, the at least one chemical species being from the group that comprises OH*, CH*, C2*, and CO2*.

3. The system of claim 1, the at least one parameter of the combustor being from the group that comprises fuel-to-air ratio, heat release rate and gas temperature.

4. The system of claim 1, wherein the system further comprises a controller that utilizes the at least one parameter of the combustor to control operation of the combustor.

5. The system of claim 4, the controller operable to control operation of the combustor by adjusting at least one fuel supply valve that feeds a fuel injection system.

6. The system of claim 1, the optical sensor optically measures and spatially resolves in three dimensions at least one chemical species within a flame produced by the combustor by collecting light from chemiluminescent emission from the flame.

7. A method, comprising:
optically measuring and spatially resolving in three dimensions at least one chemical species within a flame produced by a combustor in a gas turbine engine; and
correlating the three dimensionally measured at least one chemical species to at least one parameter of the combustor.

8. The method of claim 7, further comprising selecting the at least one chemical species from the group that comprises OH*, CH*, C2*, and CO2*.

9. The method of claim 7, further comprising selecting the at least one parameter of the combustor from the group that comprises fuel-to-air ratio, heat release rate and gas temperature.

10. The method of claim 7, further comprising controlling operation of the combustor by utilizing the at least one parameter of the combustor.

11. The method of claim 7, further comprising controlling operation of the combustor by adjusting at least one fuel supply valve that feeds a fuel injection system.

12. The method of claim 7, further comprising optically measuring and spatially resolving in three dimensions at least one chemical species within a flame produced by the combustor by collecting light from chemiluminescent emission from the flame.

13. A system, comprising:
a gas turbine engine including a combustor;
an optical sensor disposed in the gas turbine engine that optically measures and spatially resolves in three dimensions at least one chemical species within a flame produced by the combustor; and
a device that correlates the three dimensionally measured at least one chemical species to at least one parameter of the combustor.

14. The system of claim 13, the at least one chemical species being from the group that comprises OH*, CH*, C2*, and CO2*.

15. The system of claim 13, the at least one parameter of the combustor being from the group that comprises fuel-to-air ratio, heat release rate and gas temperature.

16. The system of claim 13, further comprising a controller that controls operation of the combustor by utilizing the at least one parameter of the combustor.

17. The system of claim 13, further comprising a controller that controls operation of the combustor by adjusting at least one fuel supply valve that feeds a fuel injection system.

18. The system of claim 13, the optical sensor optically measures and spatially resolves in three dimensions at least one chemical species within a flame produced by the combustor by collecting light from chemiluminescent emission from the flame.

* * * * *